United States Patent [19]

George et al.

[11] 4,195,525
[45] Apr. 1, 1980

[54] SAMPLING VALVE

[75] Inventors: David A. George, Park Forest, Ill.;
Bernard D. Strauss, Rockaway;
Irving H. Weisman, Flanders, both of
N.J.

[73] Assignee: The United States of America as
represented by the Secretary of the
Army, Washington, D.C.

[21] Appl. No.: 23,109

[22] Filed: Mar. 23, 1979

[51] Int. Cl.$^2$ ............................................. G01N 1/10
[52] U.S. Cl. ............................... 73/422 TC; 251/62
[58] Field of Search ............. 73/422 TC, 424; 251/62

[56] References Cited
U.S. PATENT DOCUMENTS

| | | | |
|---|---|---|---|
| 1,562,121 | 11/1925 | Newton | 73/424 |
| 1,837,858 | 12/1931 | Grace | 73/442 TC |
| 2,911,953 | 11/1959 | Killian | 251/62 |
| 3,034,359 | 5/1962 | Shaw | 73/422 TC |

*Primary Examiner*—S. Clement Swisher
*Attorney, Agent, or Firm*—Nathan Edelberg; Robert P. Gibson; Max Yarmovsky

[57] ABSTRACT

A fail-safe pneumatically operated by-pass sampling valve suitable for use in hazardous chemical processes utilizes a manually operated spool valve to initiate a pneumatically operated piston driven crank to rotate a sampling valve. The sampling valve withdraws a sample amount of fluid from a process line without disturbing normal process flow. A pneumatically connected spindle valve and a plurality of limiting valves are proximately positioned and operatively connected to the piston to automatically move the piston actuating member from a normally closed non-sampling position to a sampling position and then back to a normally closed non-sampling position.

10 Claims, 3 Drawing Figures

SAMPLING VALVE

GOVERNMENTAL INTEREST

The invention described herein was made in the course of a contract with the Government and may be manufactured, used and licensed by or for the Government for governmental purposes without the payment to us of any royalty thereon.

PRIOR ART STATEMENT

There are no known prior art references.

BACKGROUND OF THE INVENTION

Various means have been used in the prior art to sample fluid flowing in hazardous chemical processes used in the manufacture of explosives. The problem with prior art sampling valves was that they did not provide a fail-safe operation suitable for use in an automatic hazardous sampling system. The prior art devices could not perform the aforedescribed function while effectively eliminating metal to metal moving contact members in contact with the chemicals, eliminate the use of glass parts, prevent leakage of the chemical in any position of the valve, provide a smooth continous flow of chemical, eliminate cracks or crevices where chemicals could be trapped, sample without interrupting the flow of chemicals, and able to withstand exposure to corrosive chemicals such as nitric and sulphuric acids.

SUMMARY OF THE INVENTION

The present invention relates to a fail-safe pneumatically operated by-pass sampling valve for use in a hazardous chemical process which permits extraction of a sample on demand. The present device includes a cone type stainless steel valve having fluoroplastic sealing elements and an integral by-pass line. A remotely operated slave arm, not part of the present invention, is used to transfer a sample container from a conveyor belt to the spool valve. The container when properly positioned under the sampling port causes the spool valve to initiate the sampling cycle. The sampling valve automatically stops operating without venting the process line whenever the container is removed from the filling position.

An object of the present invention is to provide a fail-safe pneumatically operated by-pass sampling valve for use in hazardous chemical process which permits sampling of the process without interruption of the process flow of material.

Another object of the present invention is to provide a fail-safe sampling valve having no metal to metal moving contacts exposed to chemicals.

Another object of the present invention is to provide a fail-safe sampling valve which utilizes no glass parts.

Another object of the present invention is to provide a fail-safe sampling valve for a hazardous chemical process which prevents leakage of the in-process chemical in any intermediate position of the valve.

Another object of the present invention is to provide a fail-safe sampling valve for a hazardous chemical process which is capable of being remotely operated.

A further object of the present invention is to provide a fail-safe sampling valve for a hazardous chemical process which is capable of removing a sample without flow stoppage and which uses no glass parts and is able to withstand exposure to corrosive materials.

For a better understanding of the present invention, together with other and further objects thereof, reference is made to the following descriptions taken in connection with the accompanying drawings.

BRIEF DESCRIPTION OF THE DRAWINGS

Throughout the following description like reference numerals are used to denote like parts of the drawings.

DESCRIPTION OF THE PREFERRED EMBODIMENTS

Figure 1:
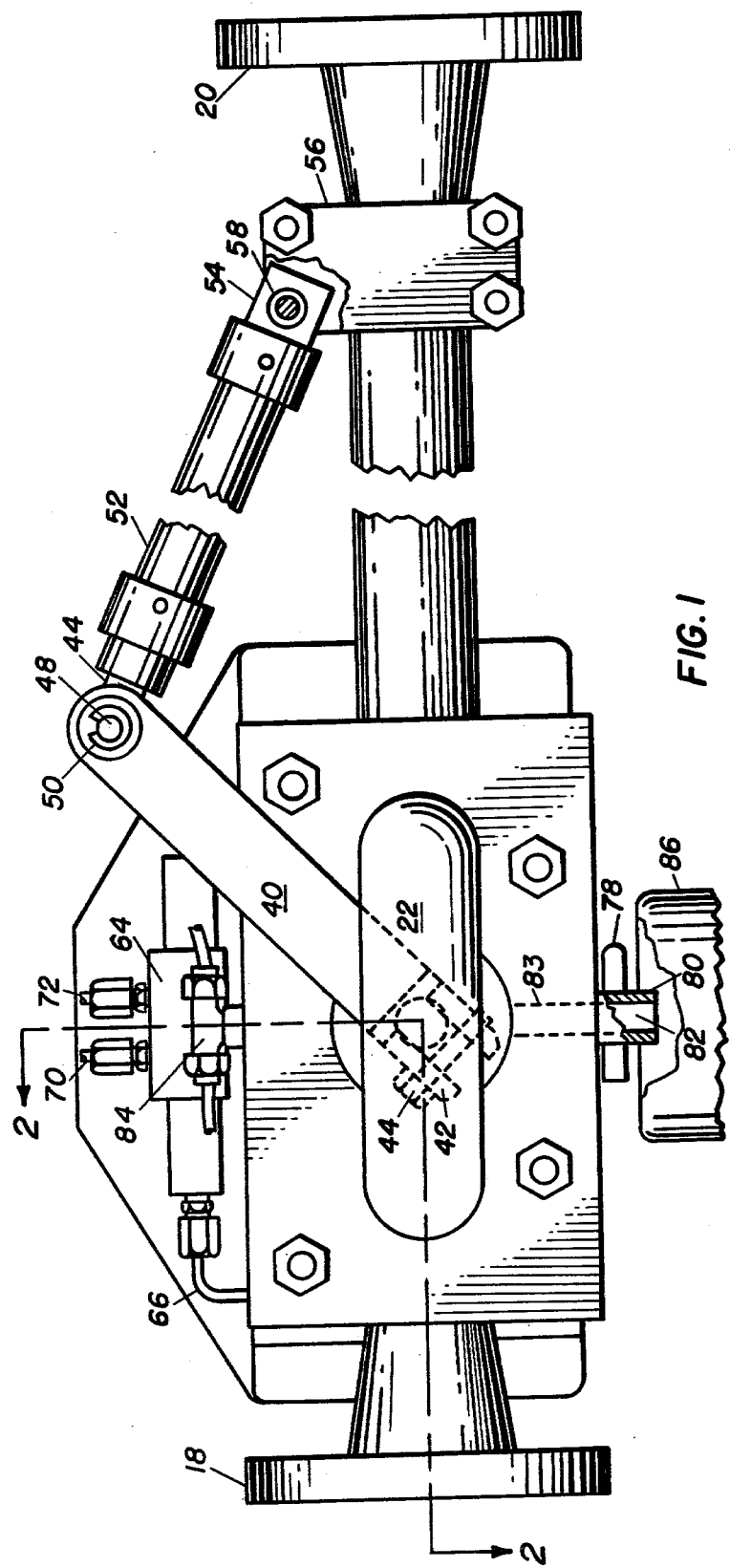
FIG. 1 is a side view of the sampling valve assembly in a non-sampling position.
Figure 2:
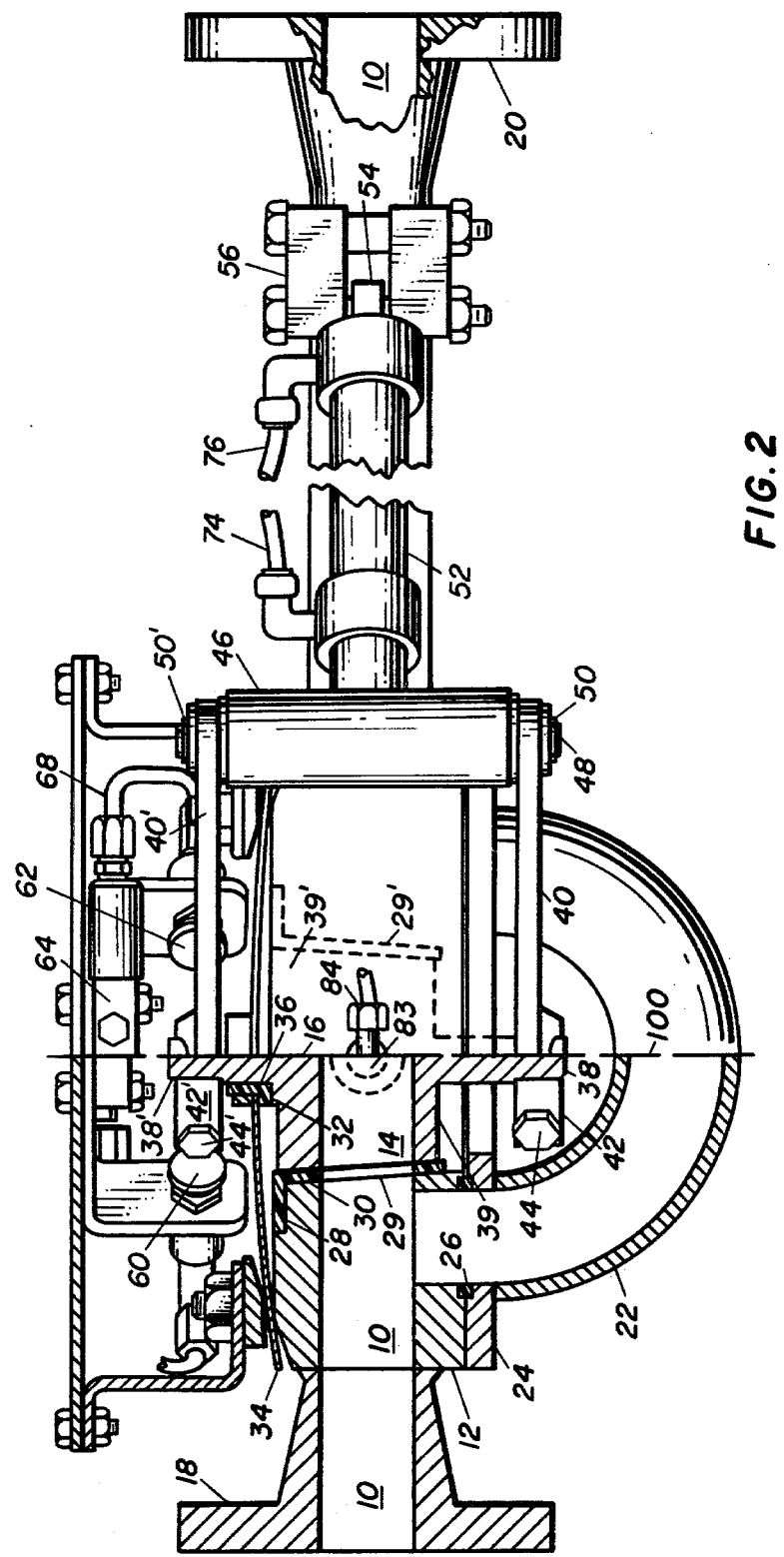
FIG. 2 is a partial cross-sectional top view of the sampling valve taken along line 2—2 of FIG. 1.

Referring now to FIGS. 1 and 2 the sampling valve assembly is shown in an out-of-limit rest position. In the out-of-limit position chemicals flow through the main channel 10 of a tubular main body member 12 and through a radially transverse main channel 14 of rotatable dispensing cone plug valve member 16. The sampling valve shown in FIGS. 1 and 2 is fixedly attached to a main pipeline, not shown, by means of first and second connecting flanges 18 and 20 respectively. The direction of flow in channel 10 is not critical to the operation of the sampling valve. A hematoroidal bypass line 22 is fixedly connected to main body member 12 by means of flanges 24 having a sealing "O" ring 26 operatively disposed therein. Only one of the flanges 24 and "O" rings 26 are shown in the drawing for purposes of clarity. A conically shaped seal element 28, having axially aligned orifices 29 and 29', therethrough, is made of fluoroplastic material which is interposed between the body housing conical valve seal 30 and the dispensing conical plug valve member 16 to prevent leakage of chemicals from housing member 12. By-pass line 22 permits flow through main channel 10 even when cone plug valve member 16 is rotated 90° to its sample dispensing position. A positive axle sealing force is maintained on conical plug valve boss 32 by a biased tension plate 34 through a fluoroplastic bearing 36. All of the main housing members metal parts 12, 18 and 20 as well as the conical plug valve 16 are made of 316 stainless steel. A pair of oppositely positioned plug valve protruding axle members, 38 and 38', are axially disposed on plug ends 39 and 39' respectively and fixedly clamped to piston crank arms 40 and 40' at forked ends 42 and 42' by bolts 44 and 44' respectively. The other ends of crank arms 40, 40' are pivotably connected to piston rod 44 by means of bushing 46 which is fixedly attached to rod 44. A pivot pin 48 rotatably passes through bushing 46 and crank arms 40, 40'. A pair of split retaining rings 50, 50' hold the pin 48, bushing 46, and crank arms 40, 40' together. The pneumatic piston cylinder 52 has its rear end 54 pivotably connected to bracket 56 at a bearing 58. A first and second normally closed pneumatic limit valve 60 and 62 are proximately positioned adjacent to crank arm 40' and responsive to motion thereof. A pneumatic double spindle valve 64 has first and second inputs 66 and 68 pneumatically connected to the output of limit valves 60 and 62 respectively. The pneumatic first and second lines 70 and 72 of double spindle valve are pneumatically connected to the rod end pneumatic line connector 74 and the piston end pneumatic line connector 76 respectively of piston 52. A spool valve actuator lever 78 is proximately disposed adjacent to sampling spout 80. Spout 80 has a dispensing passageway 82 therein which communicates on one end with the radial transverse main channel 14 of conical plug valve 16 through sampling passageway 83 in housing 12 when the cone plug valve 16 is rotated 90° from the out of limits position or normally closed non-sampling position shown in FIG. 2 to a dispensing or sampling position. When cone plug channel 14 is rotated to be in the dispensing position, air is blown through vent 84, which communicates with the other end of cone plug channel, forcing the fluid trapped in channel 14 out through spout 80 to a sampling container 86 disposed thereunder.

Figure 3:
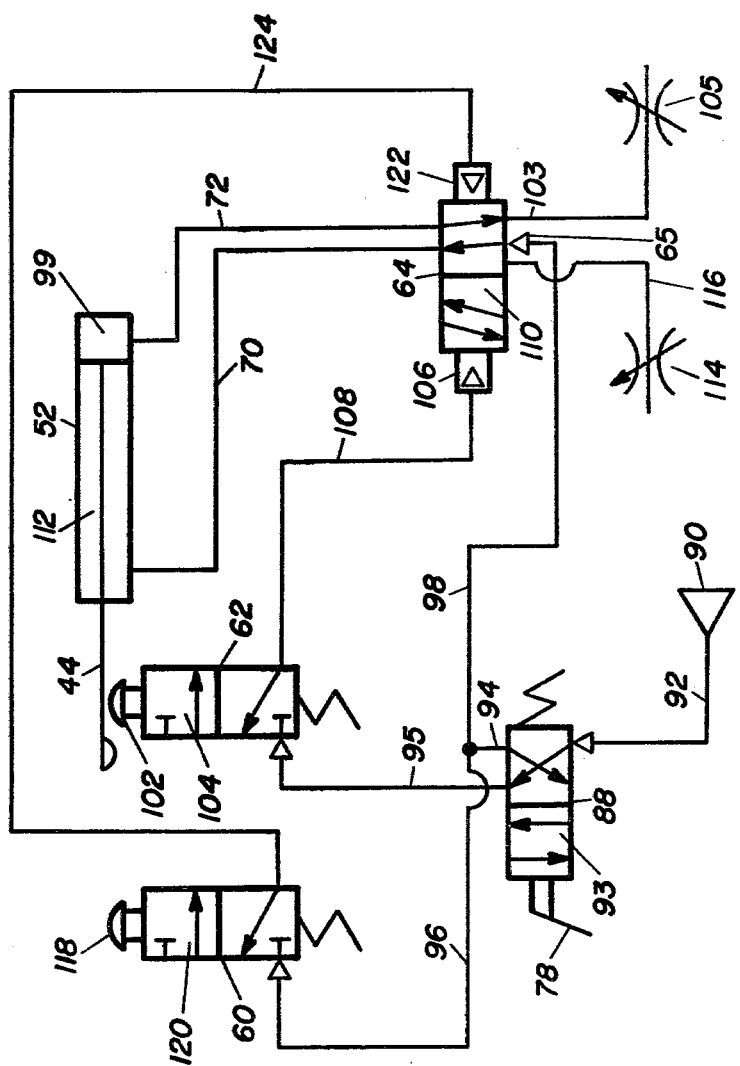
FIG. 3 is a schematic drawing of the pneumatic valves and control elements for the sampling valve.

In operation, referring now to FIG. 3, sampling occurs when a sampling container 86 is brought up over the sampling spout 80 until it contacts and lifts the actuator lever 78 which actuates a four-way, spring return, spool valve 88. Air at 80 psi enters spool valve 88 from air supply source 90 through pneumatic supply line 92 and passes through the alternate valve position 93 to the first output air line 94. Second output air line 95 is pneumatically connected to the input of the second valve 62. The air in first spool valve output line 94 flows into first branch input line 96 to a first normally closed limit switch 60, which in the non-actuated position, as shown in FIG. 3, does not permit air flow therethrough. The air in line 94 also flows into a second branch line 98 which is fed into and through input connector 65 of double spindle valve 64 to the rod end of actuating piston cylinder 52 via pneumatic first spindle valve output line 70. Piston end 99 of cylinder 52 is vented via air line 72 and 103 to the atmosphere through a first variable restriction 105. The increased air pressure in piston cylinder 52 pushes the piston rod 44 further into piston cylinder 52 causing crank arms 40, 40' to rotate plug valve 14. The crank arms 40, 40' pivot about plug axis 100 as the rod is pushed into piston cylinder 52 until the arm 40' depresses actuator button 102 of the second normally closed limit valve 62, shifting the second limit valve 62 to the alternate position 104. At this point in the cycle no further action occurs until actuator button 78 is released allowing the spool valve 88 to return to its normal position as shown in FIG. 3. In this position air is supplied through the second limit valve 62 to the left end actuator 106, via air line 108, of the double spindle valve 64, transferring this valve to the alternate position 110. When spindle valve 64 is in its alternate position 110, rod end 112, of cylinder 52 vents to the atmosphere through second variable restriction 114 via pneumatic lines 70 and 116. No sample from the pipeline could have been delivered during the above steps and the sequence would occur any time the sampling cycle was initiated with the second limiting valve 62 in the out-of-limit position as shown in FIG. 3

When the sample container 86 is once again brought up over the sampling spout 80, lifting actuator lever 78 and actuating spool valve 88, air is now transferred via air line 94 and 98 through the double spindle valve 60 alternate position 110 to the piston end 99 via air line 110 pushing the rod 44 out of cylinder 52. The arms 40 and 40' are rotated approximately 90° until the arm 40 depresses actuator button 119 of first normally closed limit valve 60 forcing it to move into its alternate position 120. The rotation of arms 40, 40' rotates conical sampling plug 16 closing the main passageway 10. An approximately 30 cc section of the main channel passageway 14, laying within the conical plug 16, is now aligned with the opening to the passageway 83 in housing 12 and to pneumatic vent 84, thus allowing the chemical within section 14 to run down the sampling spout 80 into the sample container 86. Air, or other gas, is supplied through the vent connection 84 at or above atmospheric pressure. The flow of chemical through the sampling valve assembly shown in FIGS. 1 and 2 is maintained during this sampling operation through the bypass line 22. The first limit valve 60 now in the alternate position 120 supplies air to the right end 122 of the double spindle valve 64 via air line 124 returning spindle valve 64 to the normally closed non-sampling position shown in FIGS.1–3. The air supply is now connected to the rod 44 of the cylinder 52 pushing rod 44 once again into the cylinder 52 and returning the first limit valve 60 and the double spindle valve 64 to the positions shown in FIG. 3. The cylinder 52 action continues to the limit position at which time the sampling container 86 is lowered and transferred.

Lowering the sample container 86 so that it no longer contacts actuator lever 78 at anytime during this cycle stops the action of the sampling valve.

In accordance with the aforementioned description the present invention uniquely satisfies the desired features for a sampling valve for a hazardous chemical process line which includes; the sampling of a discrete quantity of a representative sample of the chemical being processed; sampling without opening up the main line, thus preventing direct continuous discharge of chemicals; sampling without interruption of the flow of chemicals in the pipeline; and sampling during continuous flow of a chemical pipeline without providing a place for hazardous chemicals to stagnate.

While there has been described and illustrated specific embodiments of the invention, it will be obvious that various changes, modifications and additions can be made herein without departing from the field of the invention which should be limited only by the scope of the appended claims.

Having thus fully described the invention, what is claimed as new and desired to be secured by Letters Patent of the United States is:

1. Fail-safe operated bypass sampling valve for use in a hazardous chemical pipeline which comprises:
   housing means for providing a continuous flow of chemicals therethrough while extracting a sample from said chemical pipeline;
   plug means for removing a sample quantity of material from said chemical pipeline without restricting said continuous flow of said chemical pipeline;
   piston means for rotating said plug means from a normally closed non-sampling position to a sampling position and back to a normally closed non-sampling position;
   supply means for energizing said piston means;
   first valve means for connecting said supply means to said piston means when an actuator lever of said first valve means is manually actuated;
   second valve means for changing the direction of movement of said piston means from a rod-extended sampling position to a rod-withdrawn position wherein said plug means, in said rod-withdrawn position, is maintained in a normally closed sampling position; and
   third valve means connected to said supply means and said second valve means operatively positioned to be responsive to movement of moving said piston means and said plug means from a sampling position to a normally closed fail-safe sampling position.

2. A sampling valve as recited in claim 1 wherein said housing means comprises:
- a tubular main body member having a main channel therethrough, first and second connecting flanges disposed on both ends of said main body member and a conical valve seat positioned intermediate said first and second flanges;
- a hematoroidal bypass line operatively connected to said main body member for permitting continuous flow of said chemicals through said main body member when said plug means is in said sampling position; and
- means for assisting said flow of chemicals from said plug means when said plug means is in said sampling position.

3. A sampling valve as recited in claim 1 wherein said plug means comprises:
- a conical plug valve member having a radially transverse main channel therethrough, said main channel of said conical plug valve being in axial alignment with said main channel of said tubular main body member, a pair of oppositely disposed protruding axle members operatively connected to said piston means;
- seal means operatively disposed intermediate said conical valve seat of said tubular main body member and said conical plug valve member to permit flow between said main housing channel and said main channel of said conical plug valve without leakage of chemicals from main body member; and
- biasing means for providing a positive axle sealing force on said conical plug valve member.

4. A sampling valve as recited in claim 3 wherein said seal means comprises a conically shaped seal element made of fluoroplastic material having axially aligned orifice therethrough.

5. A sampling valve as recited in claim 1 wherein said piston means comprises:
- a piston cylinder having a piston end and a rod end, a piston end pneumatic line connection and a rod end pneumatic line connection, said piston end pivotally connected to one end of said main housing means; and
- crank means having one end operatively rotatably connected to said rod end of said piston cylinder, and another end fixedly connected to said pair of protruding axle members of said conical plug valve member.

6. A sampling valve as recited in claim 1 wherein said supply means comprises a pneumatic supply means for supplying air at a pressure above ambient.

7. A sampling valve as recited in claim 1 wherein said first valve means comprises a four-way, spring return, spool valve having a supply line pneumatically connected to said pneumatic supply means, and first and second output pneumatic lines, said first pneumatic line pneumatically connected to an input connector of said second valve means and to an input of said third valve means.

8. A sampling valve as recited in claim 1 wherein said second valve means comprises a double spindle valve.

9. A sampling pneumatic valve as recited in claim 1 wherein said third valve means comprises:
- a first normally closed, spring return, limit valve having an output pneumatically connected to said piston end of said piston cylinder through one end of said double spindle valve; and
- a second normally closed, spring return, limit valve having an output pneumatically connected to said rod end of said piston cylinder through another end of said double spindle valve.

10. A sampling valve as recited in claim 2 wherein said means for assisting said flow of chemicals from said plug means comprises:
- a pneumatic vent communicating with said radially transvers main channel of said conical plug valve member;
- a sampling passageway, operatively disposed in said tubular main body member, communicates with said transverse main channel of said conical plug valve member when said plug valve is in said sampling postion; and
- a spout operatively disposed in said tubular main body member and proximately positioned adjacent to said actuator lever of said first valve means, said spout conveying said sample from said chemical pipeline to a container when a container is placed under said spout and activates said actuator lever.

* * * * *